(12) United States Patent
Lacoste et al.

(10) Patent No.: US 7,591,794 B2
(45) Date of Patent: Sep. 22, 2009

(54) THERAPY PROBE

(75) Inventors: Francois Lacoste, Paris (FR); Antoine Tetard, Lyons (FR); Christian Chaussy, Allemagne (FR); Jean-Yves Chapelon, Villeurbanne (FR)

(73) Assignee: EDAP S.A., Vaulx En Velin (FR)

( * ) Notice: Subject to any disclaimer, the term of this patent is extended or adjusted under 35 U.S.C. 154(b) by 548 days.

(21) Appl. No.: 10/757,703

(22) Filed: Jan. 15, 2004

(65) Prior Publication Data
US 2005/0085726 A1 Apr. 21, 2005

(30) Foreign Application Priority Data
Jan. 14, 2003 (FR) .................. 03 00348

(51) Int. Cl.
A61H 1/00 (2006.01)
A61B 5/05 (2006.01)
A61B 8/00 (2006.01)
A61B 8/14 (2006.01)

(52) U.S. Cl. ............ 601/2; 600/411; 600/439; 600/459

(58) Field of Classification Search ........ 600/439, 600/459, 411; 601/2
See application file for complete search history.

(56) References Cited

U.S. PATENT DOCUMENTS

| | | | |
|---|---|---|---|
| 4,206,763 A * | 6/1980 | Pedersen | 600/445 |
| 5,013,312 A * | 5/1991 | Parins et al. | 606/37 |
| 5,322,055 A * | 6/1994 | Davison et al. | 601/2 |
| 5,324,299 A * | 6/1994 | Davison et al. | 606/167 |
| 5,335,663 A * | 8/1994 | Oakley et al. | 600/463 |
| 5,391,197 A | 2/1995 | Burdette et al. | |
| 5,437,283 A * | 8/1995 | Ranalletta et al. | 600/463 |
| 5,469,853 A * | 11/1995 | Law et al. | 600/463 |
| 5,471,988 A | 12/1995 | Fujio et al. | |
| 5,522,869 A | 6/1996 | Burdette et al. | |
| 5,527,331 A | 6/1996 | Kresch et al. | |
| 5,549,638 A | 8/1996 | Burdette | |
| 5,620,479 A | 4/1997 | Diederich | |
| 5,624,382 A | 4/1997 | Oppelt et al. | |
| 5,630,837 A | 5/1997 | Crowley | |
| 5,697,897 A | 12/1997 | Buchholtz et al. | |
| 5,733,315 A | 3/1998 | Burdette et al. | |
| 5,762,066 A | 6/1998 | Law et al. | |
| 5,776,092 A * | 7/1998 | Farin et al. | 604/22 |

(Continued)

FOREIGN PATENT DOCUMENTS

EP 0 446 645 A1 9/1991

(Continued)

OTHER PUBLICATIONS

International Search Report—FR 0300348.

*Primary Examiner*—Eric F Winakur
*Assistant Examiner*—Michael T Rozanski
(74) *Attorney, Agent, or Firm*—Husch Blackwell Sanders Welsh & Katz

(57) ABSTRACT

A surgical coagulation instrument having a planar ultrasound transducer without a membrane, mounted in the region of an end of a câble is provided The instrument additionally has a fluid circuit. It is useful for intra-cavity or laparoscopic treatment, without the use of the membrane. The fluid acts simultaneously as an ultrasound coupling fluid and probe cooling fluid.

19 Claims, 15 Drawing Sheets

U.S. PATENT DOCUMENTS

| | | | |
|---|---|---|---|
| 5,882,302 A * | 3/1999 | Driscoll et al. | 600/371 |
| 5,895,356 A | 4/1999 | Andrus et al. | |
| 5,938,612 A * | 8/1999 | Kline-Schoder et al. | 600/459 |
| 5,967,984 A | 10/1999 | Chu et al. | |
| 6,050,943 A | 4/2000 | Slayton et al. | |
| 6,066,096 A * | 5/2000 | Smith et al. | 600/439 |
| 6,293,945 B1 * | 9/2001 | Parins et al. | 606/45 |
| 6,379,320 B1 * | 4/2002 | Lafon et al. | 601/3 |
| 6,589,174 B1 * | 7/2003 | Chopra et al. | 600/439 |
| 2002/0188196 A1 * | 12/2002 | Burbank et al. | 600/431 |
| 2005/0004589 A1 * | 1/2005 | Okada et al. | 606/169 |

FOREIGN PATENT DOCUMENTS

| | | |
|---|---|---|
| EP | 453071 | 10/1991 |
| EP | 472368 | 6/1995 |
| EP | 983749 | 5/2005 |
| FR | 2 673 542 | 9/1992 |
| FR | 2 679 125 | 1/1993 |
| FR | 2 700 878 | 7/1994 |
| FR | 2 715 822 | 8/1995 |
| FR | 2 717 942 | 9/1995 |
| FR | 2 759 340 | 8/1998 |
| FR | 2 778 573 | 11/1999 |
| FR | 2 778 574 | 11/1999 |
| FR | 2 794 018 | 12/2000 |
| FR | 2 807 827 | 10/2001 |

* cited by examiner high-frequency ultrasound "fiber"

THERAPY PROBE

BACKGROUND OF THE INVENTION

The present invention relates to treatment of tissue by ultrasound and, more particularly, to apparatus for delivering ultrasound.

U.S. Pat. No. 6,379,320 discloses a probe for coagulating tissue by therapeutic ultrasound delivered from a planar transducer. Other ultrasound delivery apparatuses are disclosed in U.S. Pat. No. 5,630,837 which uses at least one annular piezoelectric element or U.S. Pat. No. 5,762,066 in which the piezoelectric elements are arranged in two chambers.

Focused transducers for bringing about high-temperature heating (the "HIFU" technique) are disclosed in the following French patent applications: 2,673,542, 2,700,878; 2,717,942; 2,750,340; 2,778,573; 2,778,574; 2,794,018; 2,807,827; 2,679,125; 2,715,822.

It has also been proposed to use cylindrical transducers in probes—in particular urethral probes—for producing radial emission, U.S. Pat. No. 5,391,197 states that the piezoelectric elements are cylindrical and focusing, U.S. Pat. No. 5,522,869 discloses tissue temperature measurement, U.S. Pat. No. 5,549,638 employs cylindrical piezoelectric elements and measures temperature in the tissue, U.S. Pat. No. 5,620,479 discloses tubular piezoelectric elements, U.S. Pat. No. 5,733,315 states that the piezoelectric elements are arranged around a central tube some of them being deactivated to avoid heating of the rectum. U.S. Pat. No. 5,895,356 states that the piezoelectric elements are circular and focusing. These various apparatuses have the disadvantage of the ultrasound field being diverging which can be harmful to the depth effectiveness of treatment.

Therapy transducers associated with imaging for guiding purposes are also proposed. U.S. Pat. No. 5,697,897 discloses an endoscope provided with a therapeutic ultrasound source. U.S. Pat. No. 5,471,988 discloses various endoscope configurations provided with a therapy transducer. However, in each case this transducer is focusing. The transducer is associated with an imaging transducer or optical system. U.S. Pat. No. 6,050,943 discloses piezoelectric elements having three functions: imaging, therapy and temperature control.

Vibrating instruments are also known, these comprising a transducer coupled to a tool via an ultrasound conductor. The tool can be a knife or pincer-like instrument for cutting or coagulating tissue. Coagulation results from the temperature rise of the tissue in contact with the tool, by friction. Coagulation depth depends on tissue thermal conduction and is consequently low. An instrument known as the "Harmonic scalpel" which is activated by ultrasound is marketed by the HS company, Ethicon Endo-surgery, Cincinatti, Ohio, US.

Various medical instruments employ radiofrequencies. Radiofrequency coagulators employ alternating current. An alternating current is caused to pass through the tissue, which heats up by ohmic heating. A distinction is made between bipolar coagulators (the effect is in the area between two electrodes) and monopolar coagulators (heating occurs in the immediate surroundings of the tip, the current return path being via a ground plate in contact with the patient). Endoscopic scalpels all are provided with a loop that is activated by a current and which cuts or coagulates the tissue depending on the current used. Recently, bipolar loops have appeared. Numerous other apparatuses, identified below by their commercial name, used radio frequencies:

Coagulating Intermediate Cutting (CIC, CoCut BMP) uses an HF electrode and proposes chopping coagulation and cutting periods.

Ligasure: a bipolar pincer apparatus for vessel sealing (ESVS Valleylab Boulder Colo. US). In urology this is of value for reducing time and amount of blood lost by the patient.

Laser coagulators have also been proposed using different types of laser for coagulating veins or small blood vessels.

Various applications of ultrasound to treatment are discussed in the following Articles:

| Author(s) | Title | Journal |
| --- | --- | --- |
| LAFON C; CHOSSON S; PRAT F; THEILLERE Y; CHAPELON JY; BIRER A; CATHIGNOL D | The feasibility of constructing a cylindrical array with a plane rotating beam for interstitial ultrasound application | Ultrasonics, 37(9): 615-21 2000 May |
| LAFON C. CHAVRIER F. PRAT F. CHAPELON JY. CATHIGNOL D. | Theoretical comparison of two interstitial ultrasound applicators designed to induce cylindrical zones of tissue ablation | Med Biol Eng Comput, 1999, 37: 298-303 |
| LAFON C. PRAT F. CHAPELON JY. GORRY F. MARGONARI J. THEILLERE Y. CATHIGNOL D. | In vivo effects of interstitial ultrasound plane applicator on Dunning tumors | IEEE, 1998, 2: 1423-1426 |
| LAFON C. PRAT F. CHAPELON JY. GORRY F. MARGONARI J. THEILLERE Y. CATHIGNOL D. | Cylindrical thermal coagulation necrosis using an interstitial applicator with a plane ultrasonic transducer: in vitro and in vivo experiments versus computer simulation | |
| LAFON C. CHAPELON JY. PRAT F. GORRY F. THEILLIERE Y. CATHIGNOL D. | Design and in vitro results of a high intensity ultrasound interstitial applicator | Ultrasonics, 1998, 36: 683-687 |
| LAFON C. CHAPELON JY. PRAT F. GORRY F. MARGONARI J. THEILLIERE Y. CATHIGNOL D. | Design and preliminary results of an ultrasound applicator for interstitial thermal coagulation | Ultrasound in medicine & biology, vol. 24, n°1, 113-122, 1998 |

-continued

| Author(s) | Title | Journal |
|---|---|---|
| LAFON C. THEILLERE Y. PRAT F. AREFIEV A. CHAPELON JY. CATHIGNOL D. | Ultrasound interstitial applicator for digestive endoscopy: in vivo destruction of bilary tissues | IEEE, 1999, 2: 1447-1450 |
| LAFON C. THEILLERE Y. PRAT F. AREFIEV A. CHAPELON JY. | Development of an interstitial ultrasound applicator for endoscopic procedures: animal experimentation | Ultrasound in medicine & biology, vol. 26, n°4, 669-675, 2000 |
| LAFON C; CHAPELON JY; PRAT F; GORRY F; MARGONARI J; THEILLERE Y; CATHIGNOL D | Design and preliminary results of an ultrasound applicator for interstitial thermal coagulation. | Ultrasound Med Biol, 24(1): 113-22 1998 Jan |
| PRAT F. LAFON C. MARGONARI J. GORRY F. THEILLERE Y. CHAPELON JY. CATHIGNOL D. | A high-intensity US probe designed for intraductal tumor destruction: experimental results. | Gastrointestinal endoscopy, 1999, 50(3): 388-392 |
| PRAT F. LAFON C. THEILLERE Y. FRITSCH J. CHOURY AD. LORAND I. CATHIGNOL D. | Destruction of a bile duct carcinoma by intraductal high intensity ultrasound during ERCP. | Gastrointestinal endoscopy, 2001 Jun, 53(7): 797-800 |
| LAFON C.; MELO DE LIMA D.; THEILLERE Y.; PRAT F. CHAPELON JY; CATHIGNOL D. | Optimizing the shape of ultrasound sound transducers for interstitial thermal ablation | Med. Phys. 29 (3), March 2002. |

Known devices raised certain problems which are not necessarily identified in the state-of-the-art.

Limit Risks of Hemorrhage

The surgeon is always faced with the problem of hemostasis. He should coagulate the vessels during surgery and ensure they will remain sealed after intervention. Arterial bleeding is frequently easy to identify as blood flows is pulsed. Veins are problematic because they can be difficult to seal. The danger of bleeding is particularly serious in endoscopic surgery because it is more difficult to master.

Reduce Risk of Glycine Resorption

Endoscopic surgery is frequently performed in aqueous medium: saline solution or glycine; glycine is a liquid used during endoscopic surgery; it is an electrical insulator. When pressure increases, glycine can be resorbed by the patient's venal system which can lead to the so-called TURP syndrome. This is a reason why, during endoscopic surgery (of the prostate, endometer) the amount of electrolyte in the blood is monitored and duration of treatment is limited. For these reasons also, it is important to successfully coagulate the veins.

Limit Risk of Recurrence

During cancer surgery, the insertion of a surgical instrument introduces a risk of spreading tumor cells in the organism. In bladder cancer for example, it is suspected that the simple fact of touching the tumor can increase the risk of recurrence. It would consequently be useful to coagulate tissue remotely without touching it.

Be Selective

Conventional instruments have the same effect whether the tissue is normal or tumor. One consequently looks for an instrument which could selectively destroy certain tissue, for example tumor tissue.

SUMMARY OF THE INVENTION

In some of its various embodiments, the invention provides a solution to one or several of these problems.

Therefore, the invention provides a laparoscopy probe having at least one planar transducer. Preferred embodiments comprise one or several of the following features:

the probe body has a channel for inserting an ultrasound angiography probe;

the probe has a plurality of transducers and a flexible or articulated body;

the probe has a channel that opens in the region of said transducer, adapted to transmit a partial vacuum;

the opening of said channel surrounds the transducer.

The invention also provides a coagulation apparatus having an ultrasound transducer and a scalpel blade movable with respect to said transducer. In an embodiment, the apparatus further has an imaging transducer.

The invention further provides a coagulation instrument having a planar ultrasound transducer without a membrane, mounted in the region of an end of a cable. In an embodiment, the coagulation instrument has a diameter less than 1 to 5 mm. In another embodiment, the cable is flexible.

The invention furthermore provides an endoscopic apparatus comprising the above instrument and a cooling and coupling fluid circuit, with fluid inlet and outlet openings preferably in the region of the transducer.

Other characteristics and advantages of the invention will become more clear from the description which follows of some embodiments of the invention provided solely by way of example with reference to the attached drawings.

DETAILED DESCRIPTION OF THE INVENTION

Figure 1:
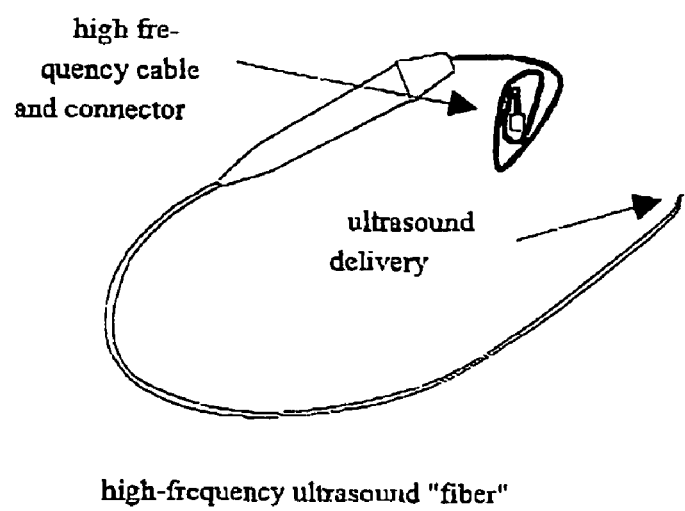
FIG. 1 is a diagrammatic view of an endoscopic coagulation instrument.

In a first embodiment, the invention employs a planar transducer for endoscopic coagulation. The transducer is used without a separating membrane, coupling as well as cooling being provided by the liquid surrounding the organ to be treated. The instrument is fitted with a cable at the end of which the transducer is mounted. The transducer is powered via the cable. It is flexible to be able to be inserted in endoscopic apparatus; the cable can be rigid or partially rigid if it is simultaneously to provide forward-and-back or rotary guiding of the transducer. FIG. 1 is a schematic diagram of one example of the instrument: a transducer is mounted at the end of a flexible cable. The complete assembly is of relatively small (fiber size) diameter to allow it to pass in the operating channel of an endoscope, a needle, a cytoscope or the like, its diameter being 1 to 5 mm. Like the prostate probe, the transducer can be mounted laterally or at the end in order to direct the field substantially along the axis.

In view of the small dimensions, it is preferable to choose a high-frequency (8-20 MHz) transducer, to ensure the field does not diverge.

Cooling and coupling liquid circulation can be provided by the circuits conventionally provided in endoscopic apparatus. An inlet circuit terminates close to the transducer; an outlet circuit is also provided for drawing off or receiving liquid. The settings of the openings can allow the liquid flow to be directed. The liquid simultaneously provides cooling and ultrasound coupling.

The absence of a membrane facilitates insertion and improves coupling with the organ or tissue to be treated by eliminating one interface and ensuring that the liquid extends continuously between the transducer and the tissue. All windowing is also avoided so that vision (in the case of endoscopy) is not limited; nor is the treatment region limited by a window.

In one needle or interstitial coagulator application, the apparatus of FIG. 1 is employed. Unlike the case of FIG. 2, the "fiber" is inserted into a needle. Such a coagulator can be employed for treating:
  bone metastases
  the liver
  pulmonary tumors. This is particularly interesting as, since the ultrasound is stopped by air, a selective effect on the (solid) tumors compared to healthy pulmonary tissue (formed of air-filled alveoli) which is not affected, is obtained.

Figure 2:
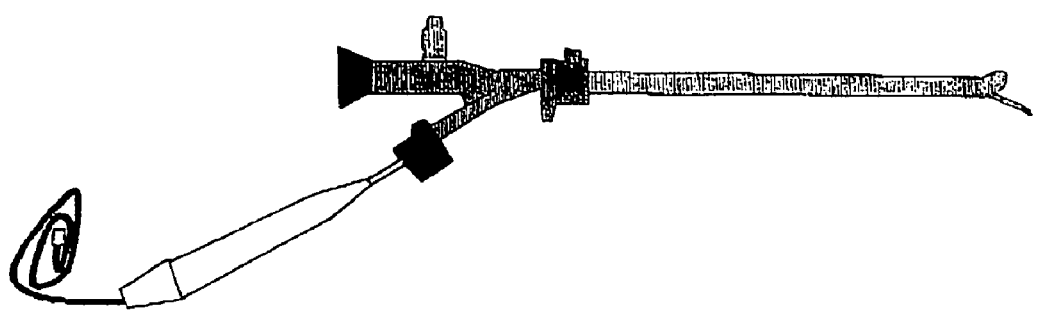
FIG. 2 is a diagrammatic view of an endoscopic apparatus using the instrument of FIG. 1.

FIG. 2 shows one example of a coagulator in an endoscopic apparatus—in the example a cytoscope. It will be understood that rigidity of the cable is not essential in such apparatus. Clinical applications of endoscopic coagulation are as follows:
  tumors of the bladder after resection of polyps or of the main tumor. The apparatus serves to sterilize the operating field in order to avoid local recurrence;
  tumors of the bladder, for coagulating regions of vesicle mucus located by tumor imaging means, for example by fluorescence;
  digestive system tumors, for example rectal polyps, like for the bladder;
  pulmonary tumors, as explained below.

FIGS. 3 to 8 show a second embodiment. This apparatus is adapted for prostate treatment; it comprises an endo-urethral probe with a planar transducer and a small balloon close to the end. The balloon allows the device to be anchored in the bladder, by inflating a balloon after insertion. This ensures the probe is correctly positioned with the transducer at the prostate; optionally, the liquid in the balloon can also be cooled thereby protecting the bladder and the sphincter. One can, like in the example of FIGS. 1 and 2, use a membrane-less transducer; one can also use a separate circuit for inflating a balloon and for cooling the transducers.

Figure 3:
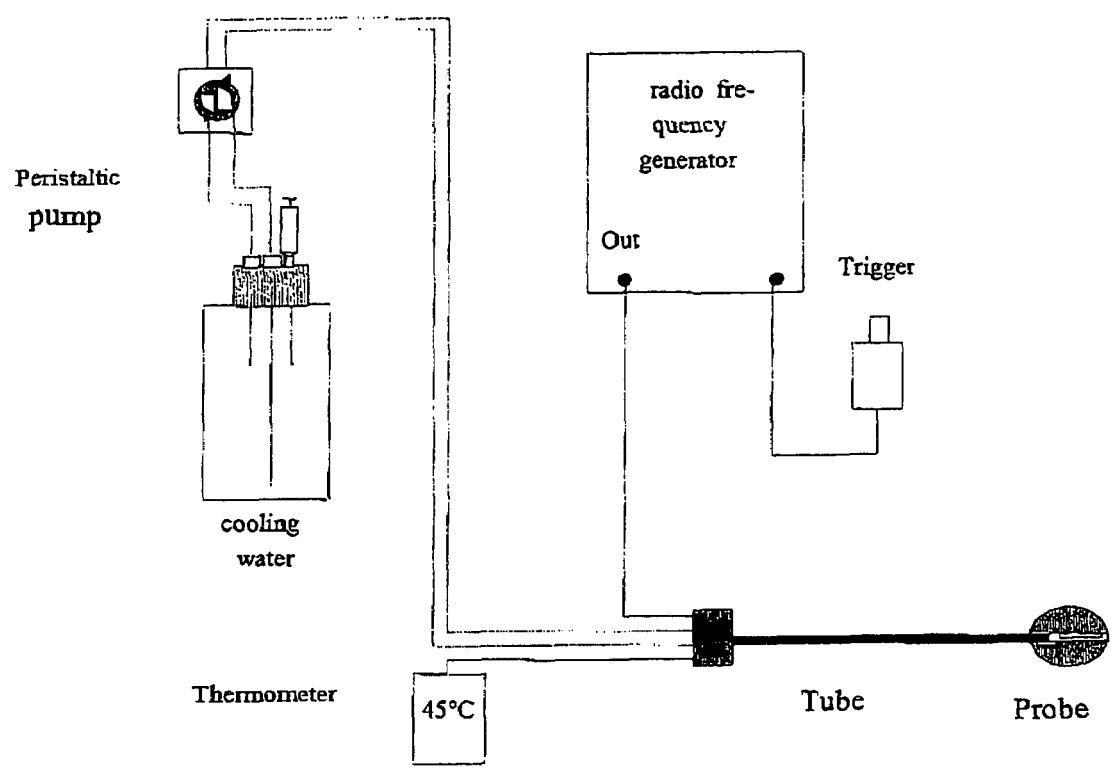
FIGS. 3 and 4 are diagrammatic views of prostate treatment apparatus.

FIG. 3 is a diagrammatic view of the complete apparatus, with a probe. The balloon inflation circuit is not shown. FIG. 3 shows, notably, the probe which can be seen in FIG. 4. FIG. 3 shows a housing for the electronics to which one of the probes described in the FIGS. below can be connected.

Figure 4:
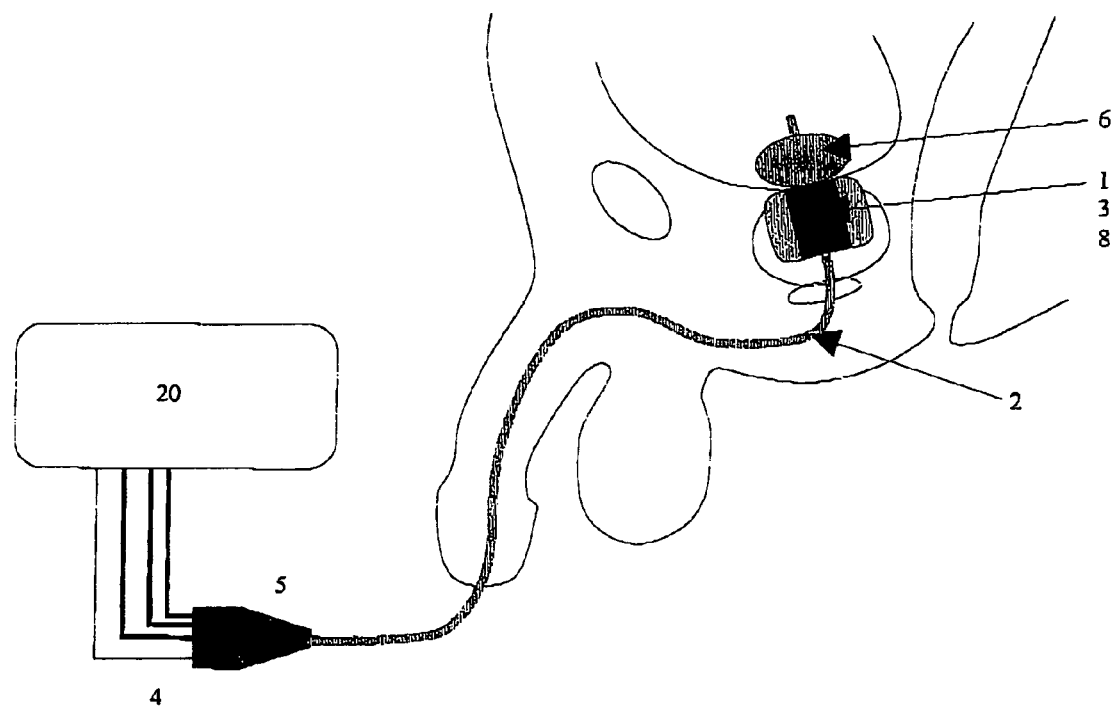

FIG. 4 shows another diagrammatic view of the apparatus. The housing 20 includes the electronics and cooling circuit. It includes various buttons and lamps on the front panel for controlling the ultrasound power to be delivered, the flow rate and temperature of the cooling circuit. This figure shows the balloon 6, the probe body 2 with the coupling and/or cooling liquid conduits, connected to the housing. The prostate can also be seen, with the region that is being heated. Either alternatively or together, the balloon, the transducer(s) or the wall of the probe in line with the transducers or upstream or downstream of the transducers, can be cooled.

Figure 5:
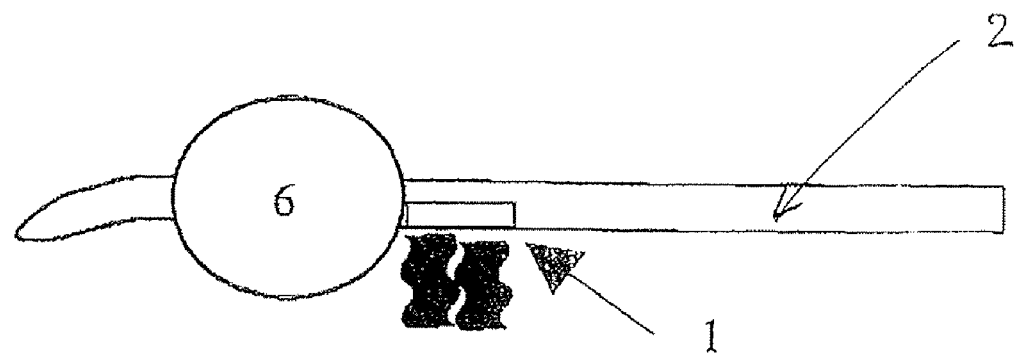
FIGS. 5 to 8 are examples of probes for the apparatus of FIGS. 3 and 4.

FIG. 5 shows the probe; it is formed by a catheter comprising:
  a planar ultrasound transducer 1, or a transducer which delivers a planar wave at its distal end,
  the conduits 2 for the coupling and cooling liquid,
  optionally, a temperature sensor such as a thermocouple for ensuring that the transducer does not overheat; prostate temperature can also be measured locally;
  in its proximal portion, connectors for the liquid, and powering of the transducer and temperature probe;
  optionally, a mechanical interface located in the connector provides for rotation of the probe about itself;
  a balloon at its end for positioning the probe with respect to the vessel neck; The advantage is that the balloon ensures the probe stays in place in the urethra;
  optionally, a sterile probe sheath in a flexible material, should the transducer not be used without a membrane.

Figure 6:
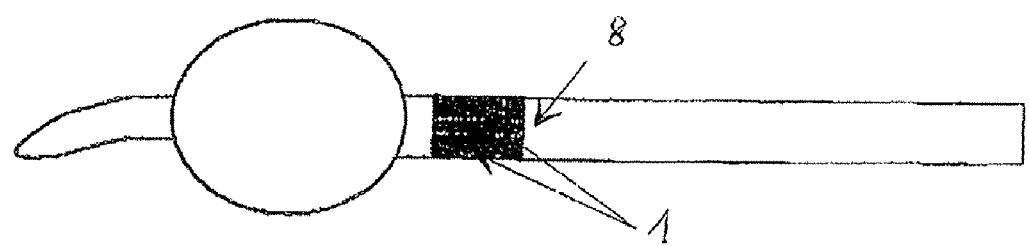

In the example of FIG. 6, an imaging transducer 8 is provided, mounted in a mechanical relationship with the planar firing transducer 1; the advantage is that the treated tissues can be imaged. The imaging transducer operates at an acoustic power well below that of the planer firing transducer, and does not have a notable tissue heating effect. Optionally, the firing and imaging functions are provided by one and the same transducer which is alternately connected to an echography-type electronic circuit (for sending and receiving pulses) and to a radiofrequency power generator. This saves on space; since the image is in the same plane as therapy, the therapy can be controlled accurately.

Figures 7A, 7B:
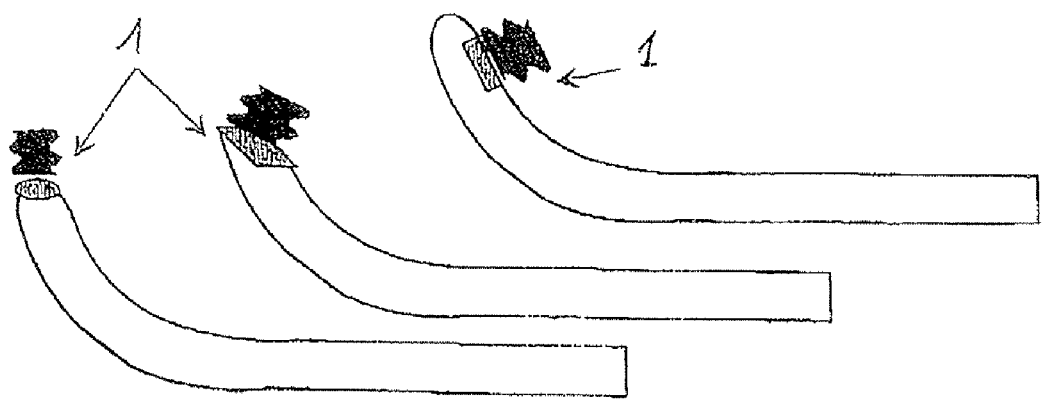

FIGS. 7A and 7B shows that the height of the arrangement of planar transducers 1 can be adapted to the region to be treated. Several designs of probe are proposed:
  depending on the size of the prostate, a transducer of varying length can be selected,
  if it is desired to treat the lateral lobes, a side-emitting transducer, mounted laterally, can be selected as shown in FIG. 7B;

for treating the median lobes, a front-emitting transducer is selected as shown in FIG. 7A;

to perform the thermal equivalent of vessel neck incision, a narrow transducer will be used.

For use, the surgeon will choose that probe which is best adapted to the patient. The probe, connected to the electronics housing is introduced into the urethra. The surgeon can employ various techniques for guiding the probe: the probe is inserted like any other urethral probe and held in position by the balloon which is inflated in the bladder, at vessel neck level. The surgeon can check probe position using transrectal ultrasound imaging, or abdominal or transurethral ultrasound imaging. In the latter case, the probe will also include an imaging transducer, for example integral with the firing transducer, as shown in FIG. 6. The surgeon will send "shots" towards the prostate. Advantageously, some 20 shots are fired, the probe being rotated about itself between shots.

The follow-up to operation is simple. Coagulation can be followed by ablation of the coagulated tissue, using a conventional instrument or the apparatus sold under the name Rotosect by Karl Storz. As the tissue is coagulated, hemorrhaging is limited and the conventional instrument operates more simply, better controlled by the surgeon.

The following alternative embodiments are possible:

two transducers back to back. The two transducers are mounted in a common chassis and arranged back-to-back. Emission consequently takes place simultaneously in two opposite directions, which speeds up treatment correspondingly. For example, the right and left lobes of the prostate can be treated simultaneously.

a transducer emitting at both sides. The same transducer can be used, thereby taking advantage of the two emission faces.

Similarly, multiple transducers can be arranged with the electric circuit being in parallel.

A flexible mechanical assembly for introduction into the prostate is preferred. A transducer of considerable length can also be divided into several shorter transducers aligned along the axis of the catheter, but mounted on a flexible support, as discussed below.

Figure 8:
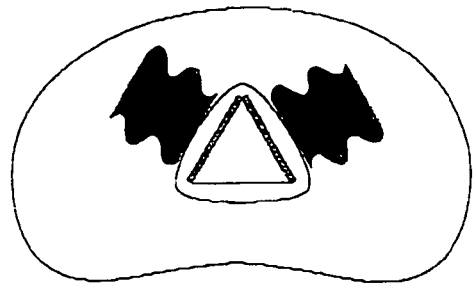

FIG. 8 shows one example of a shaped urethral probe. To control rotational positioning of the probe about itself, it can have a non-circular shape and follow the shape of the urethra. For example, in cross-section, the urethra has frequently a triangular shape, the base of the triangle being at the posterior portion. Advantageously, two transducers can be arranged which will deliver acoustic energy towards the lateral lobes, as shown in FIG. 8. If the probe-carrying catheter has a similar shape, it will not turn during insertion and the surgeon can be sure of the orientation of the transducer. The transducer could also be arranged to rotate inside the probe body which remains stationary. The advantage is again good control of rotary positioning of the transducer.

The probe sheath can be left in place after treatment. Thermal tissue treatment and in particular treatment of the prostate generally causes edema with the result that the patient frequently experiences urinary retention after treatment. The sheath is chosen to be of a material and have a thickness such that it plays the part of an endourethral prothesis or stent, pushing back treated tissue.

The apparatus is adapted for non-invasive, non-surgical treatment of benign prostatic hyperplasia (BPH). Compared to other non-invasive treatments of the prostate, the advantages are:

low cost of apparatus and consumables
fast treatment
possibility of treating median lobes
possibility of simulating incisions (small prostates, young patients).

With reference to FIGS. 9-12, we shall describe a third embodiment of the invention. Like in the first embodiment, the coagulator operates without a membrane. The apparatus performs tissue necrosis and vessel coagulation by collimated (plane wave) ultrasound, aimed at non-hemorrhagic surgery.

This apparatus can be used by urethral route for pathological prostate tissue treatment; a small balloon could then be provided as described above;

in hysteroscopy for endometrial resection: endometer pathology, polyps, intra-uterine fibromas;

in pneumology for pulmonary tumor treatment. The advantage in this case is ultrasound selectivity: the latter will penetrate into the tumors but not into healthy tissue in view of the honeycomb-like structure of the latter.

The apparatus can coagulate the paranchime as well as vessels. The aim of this coagulation tool is to save on time for resection, and limit risks. Coagulation is more effective than when radiofrequency resection apparatus is used as the energy is delivered at a greater depth. All the adenoma regions of the prostate (or organ to be treated) are directly or indirectly coagulated by necrosis of the vessels irrigating them.

The advantages are:

significant reduction in bleeding, with resulting better visibility of the operating field. The long resection technique learning curve is shortened;

reduction in complications through hemorrhaging;

reduction in patient glycine absorption: the liquid is not in contact with unexposed vessels and intervention yield is better (the amount of tissue removed is optimized per unit of time as hemostatis occurs more deeply);

in the case of the prostate, improvement in long term efficiency of resection where urologists fear complications. Indeed, the quantity of pieces of adenoma tissue removed can be greater than those in conventional procedures where the time spent on hemostatis is not negligible;

saving on time.

Figure 9:
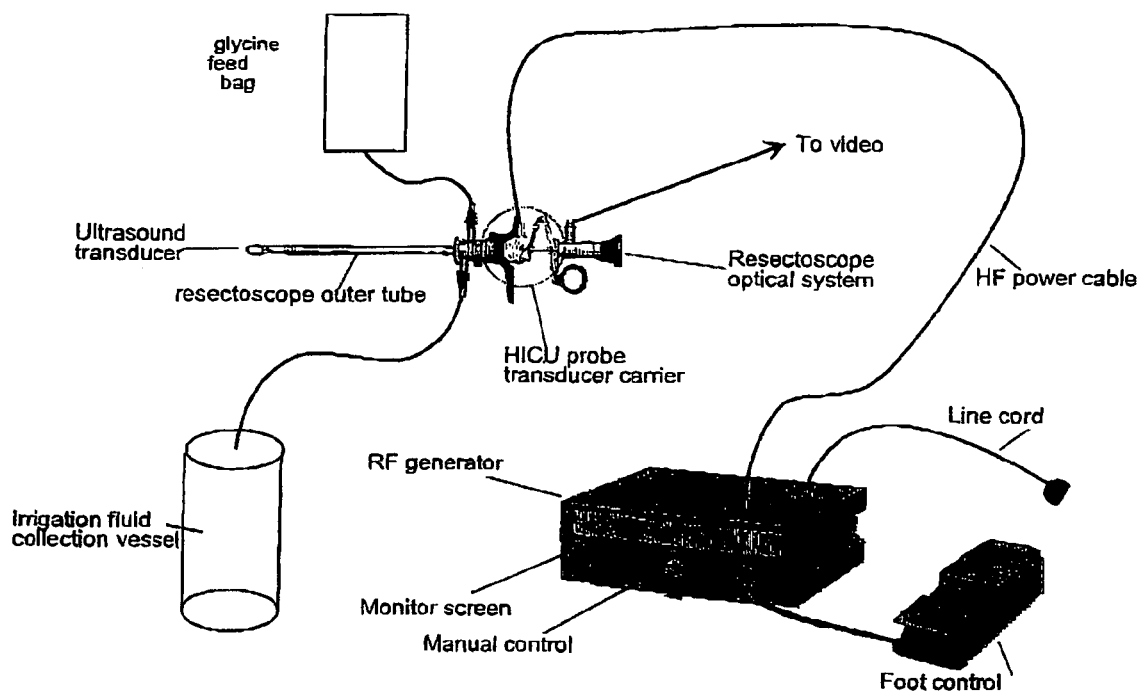
FIGS. 9 to 16 are diagrammatic views of coagulation and cutting instruments.

In a first example, the device has no resection cutter. It comprises ultrasound delivery means connected to a housing with the electronics. The housing contains the HF power electrical signal generation and control circuits. The delivery means are designed to be brought into contact with the tissue to be treated under optical monitoring. FIG. 9 shows an example of the arrangement. Like in the first embodiment, the device does not include a membrane or a window transparent to ultrasound. Transducer cooling is provided by the rinsing liquid. Acoustic coupling is also provided by this liquid or, intermittently, directly by contact between the transducer and the tissue. The advantage of eliminating the membrane is greater visibility of the operating field and simplification of the apparatus.

The sterile or sterilizable delivery means are adapted for use on rectoscopes. Coagulation is performed with visual monitoring. The tool coagulates adenoma tissue and vessels irrigating the prostate in the intermediate region. Changeover from coagulation to resection and vice-versa is very easy and very fast.

Figure 10:
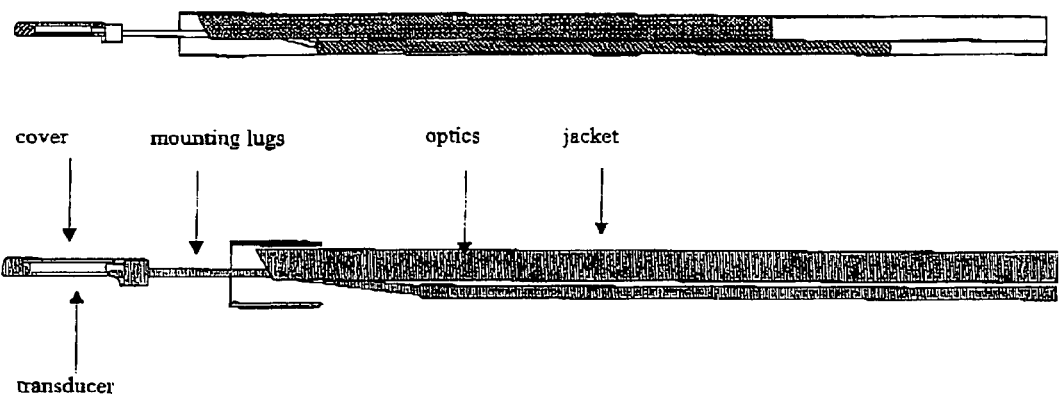
Figure 10:
Figure 11:
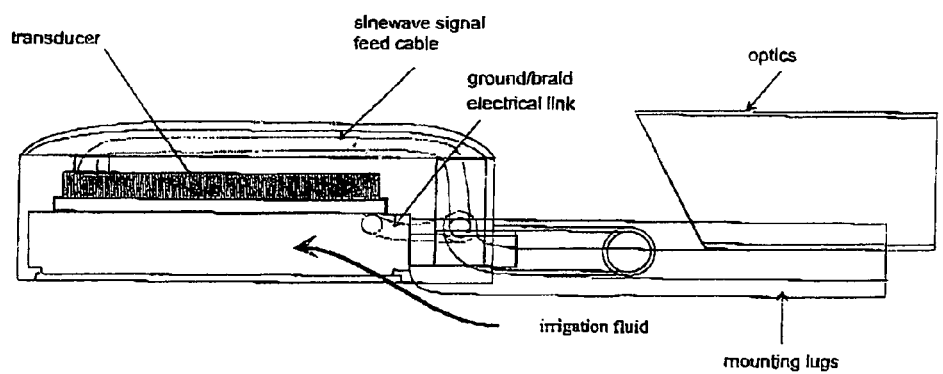
Figure 12:
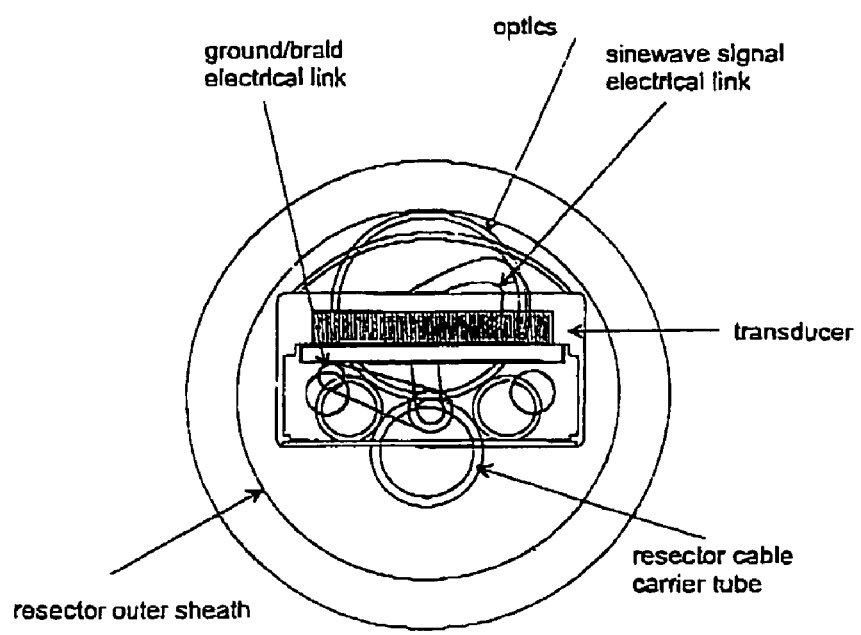
Figure 13:
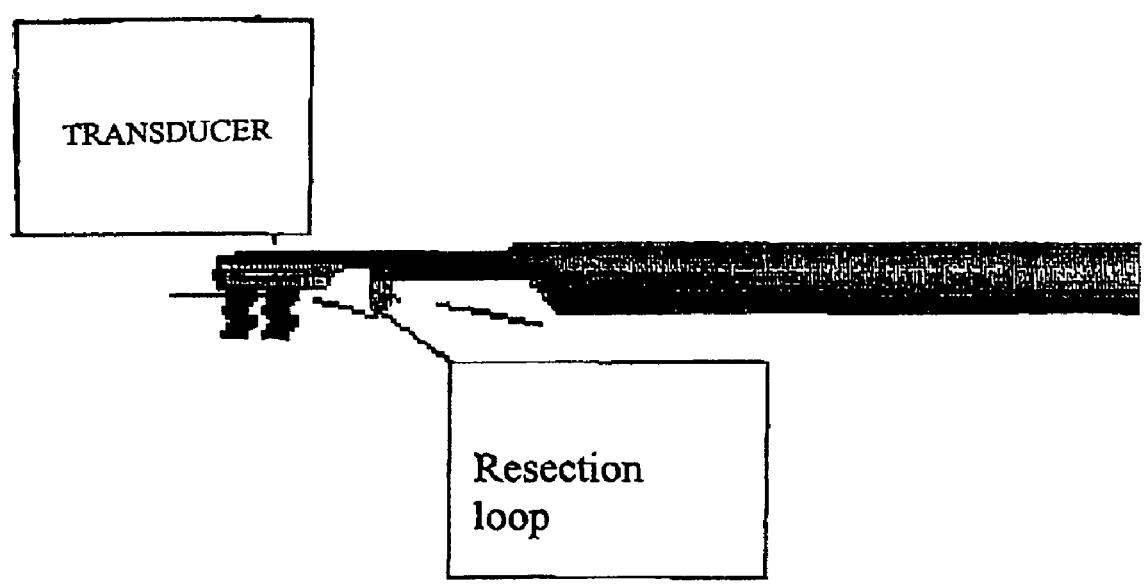

FIGS. 10, 11 and 12 show details of the applicator. The transducer is mounted in housing means themselves secured onto the optical system or onto a member on which the optical system is secured, using securing lugs in an arrangement which does not shade the field. It can be seen from FIG. 12 that the assembly is sufficiently small to be integrated into the outer sheath of the resection tool. The irrigation liquid can be directed towards the transducer to ensure cooling and acoustic coupling.

Optionally, the securing lugs are hinged so that the ultrasound beam can be directed parallel, obliquely or along the axis of the instrument. The transducer can perform a to-and-fro movement on the instrument axis in the same way as a resection loop.

In a second example, the device has, apart from the planar transducer, a resection loop. The surgeon can select tissue coagulation before or after resection. The transducer is mounted in addition to the resection loop, the advantage being that the same instrument performs resection and deep coagulation. The resection loop cuts and the transducer coagulates.

The transducer can be mounted either:
integrally with the resection loop and downstream thereof;
upstream of the loop,
integrally with the body of the resection tool in which case it remains fixed while the resection loop performs a to-and-fro motion.

Numerous constraints can be taken account of in the design of an ultrasound coagulation resection tool:
space available inside the outer tube of the resection tool and ahead of the resection loop;
preservation of the space reserved for irrigation;
when imaging is provided, preservation of the surgeon's visual field and;
the fact of placing the transducer ahead of the resection loop can also create difficulties in bringing the loop into contact with the tissue to be removed (mechanical problem).

Figure 14:
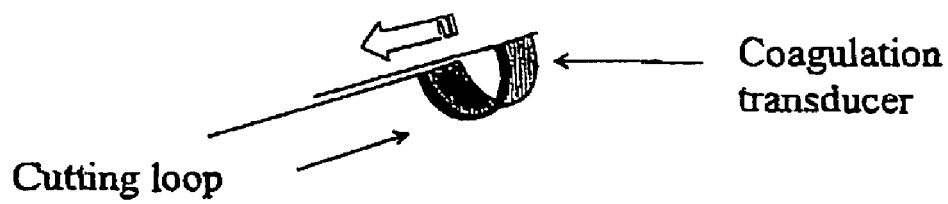

FIG. 14 shows a position which takes account of some of these constraints; the transducer is arranged right along the loop, with a very low firing depth, with a scalpel blade at the edge of the transducer.

Figure 15:
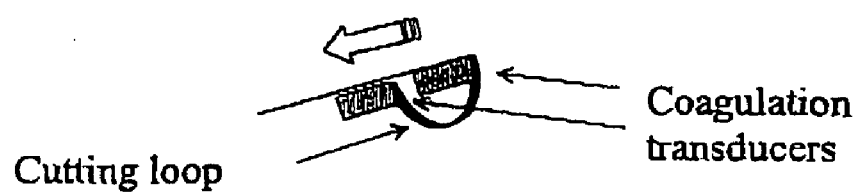
Figure 16:
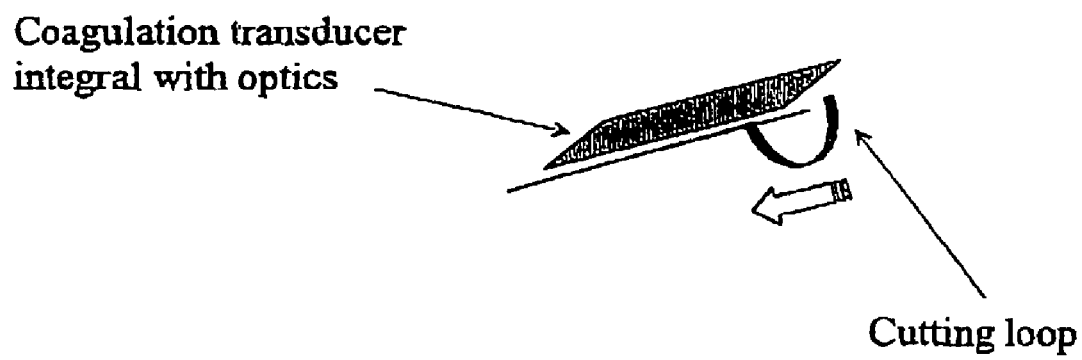

FIG. 15 shows an example in which the transducer has two transducer elements attached to arms. Two transducers for example 2 mm wide and 5 mm long, are located at each side of the resection loop, attached to retention arms in order to free the mid-field. This consequently keeps the field of vision clear around the resection loop.

In one alternative embodiment, the transducer emits downwards and acoustic coupling is via the rinsing liquid; there is consequently no balloon, membrane or window. The transducer is integral with the resection tool body and the resection loop is movable with respect to the transducer.

Depth of shots and speed of displacement: accuracy of surgical intervention is extremely important, for example in the case of the prostate when one approaches the sphincter. Depth of "shooting" can be adapted without changing transducer, by adapting time and/or frequency of shooting. Coagulation depth, during movement, is adjustable between preferably 1 and 3 mm, without change of coagulation tool.

Regarding wiring, ideally, the transducer and coagulator are wired to the same power network, controlled by the same foot pedal, the generator responsible for coagulation being arranged in parallel on the habitual generator, each operating at its frequency and being relatively insensitive to the frequency of the other. A T-junction on the resection loop power cable enables the ultrasound transducer excitation current to be fed into the same cable as that for the resection loop. At the distal end, the two circuits can be split by suitable electronics, for example resonant circuits or filters only allowing the passage of each tool's operating frequencies. This has the advantage of reducing bulk and amount of wiring.

Figure 17:
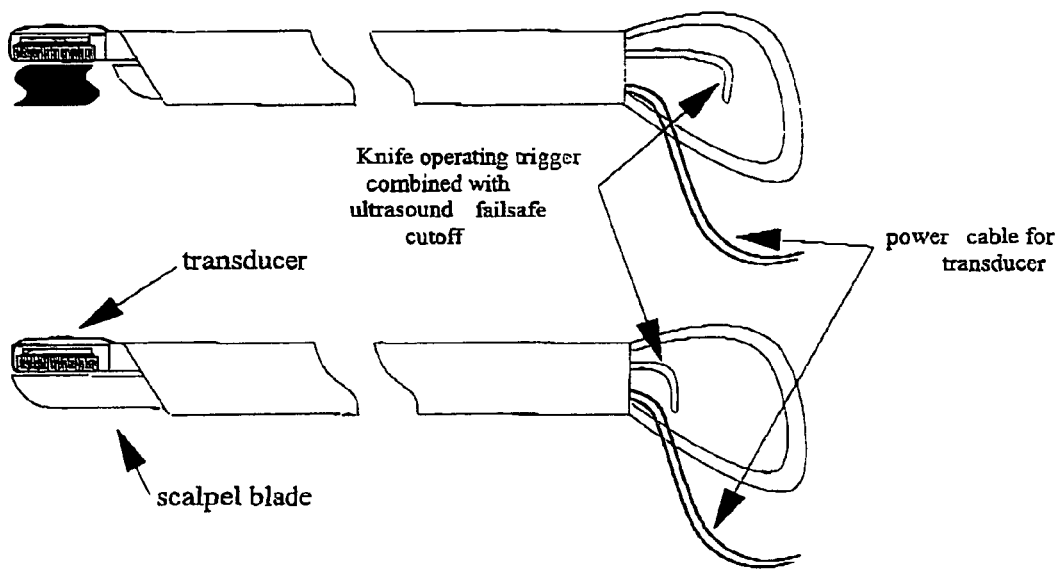
FIGS. 17-19 are diagrammatic views of a scalpel/coagulator.

In a fourth embodiment, a coagulator/scalpel is provided. It consists of an ultrasound coagulator associated with a scalpel as shown in FIG. 17. First, the surgeon coagulates the vessel using the ultrasound beam. Next, he can cut the vessel by advancing the cutting blade. During cutting, the transducer can be pressed against the vessel thereby avoiding the need to hold it between two gripping jaws. The transducer can operate with or without a membrane depending on the application.

Figure 18:
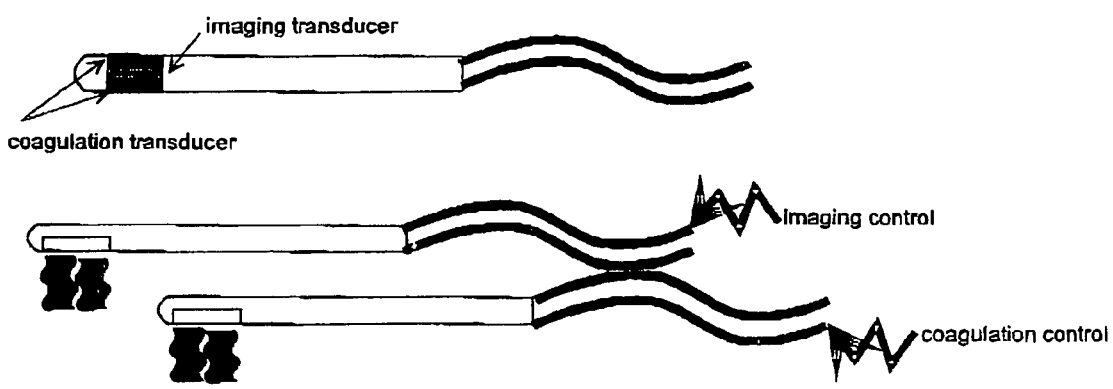

In the example of FIG. 18, an imaging transducer is also provided.

Figure 19:
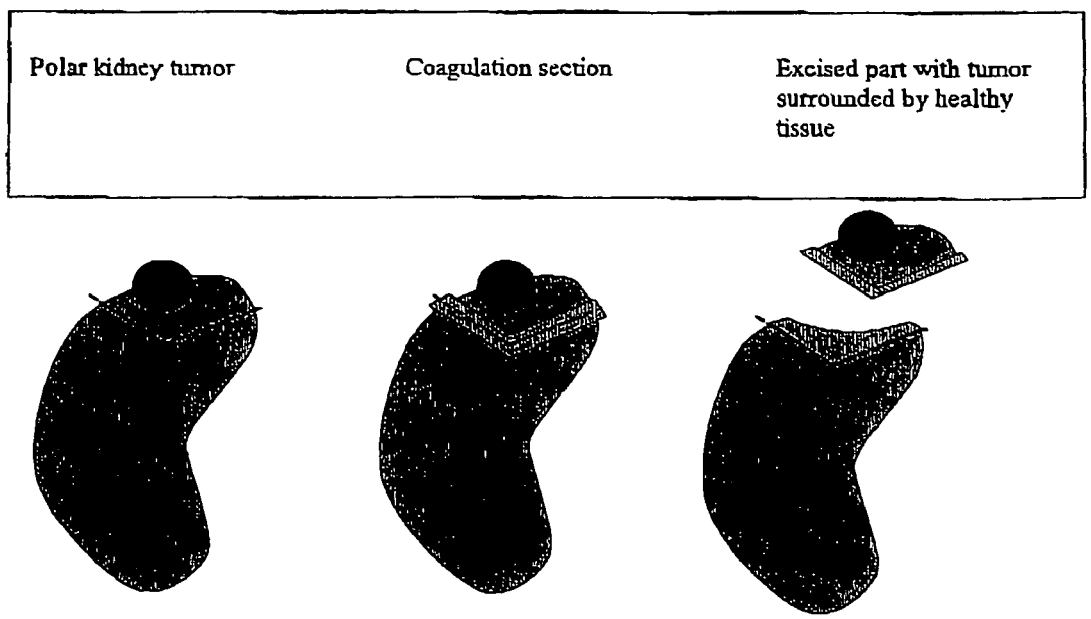

The aim of this coagulation tool is to be able to perform more readily partial nephrectomy in particular for laparoscopy. Partial kidney ablation is currently rarely practised using laparoscopic techniques due to the significant vascularisation of the organ. As there is a high risk of hemorrhaging, laparoscopic intervention is more dangerous. The coagulation accessory allows this intervention to be performed using laparoscopy and limits the time needed to perform vessel suturing. The sterile or sterilizable applicator is inserted into a trocar. Coagulation is performed with visual observation. The tool coagulates the renal parenchyma and the vessels passing therethrough in a section allowing the tumor to be isolated as FIG. 19 shows for the case of a polar tumor of the kidney.

The part that contains a tumor is excised after cutting on the coagulation section. Normal pathological analysis can be performed provided a sufficient margin has been allowed between the tumor and the renal parenchyma section. Expected benefits for the patient are those of partial nephrectomy and those of laparoscopic surgery, compared to ablation of a kidney in open surgery. For one type of given surgery, the advantages are:
reduced duration of intervention,
reduction in per-operative bleeding.

Figure 20:
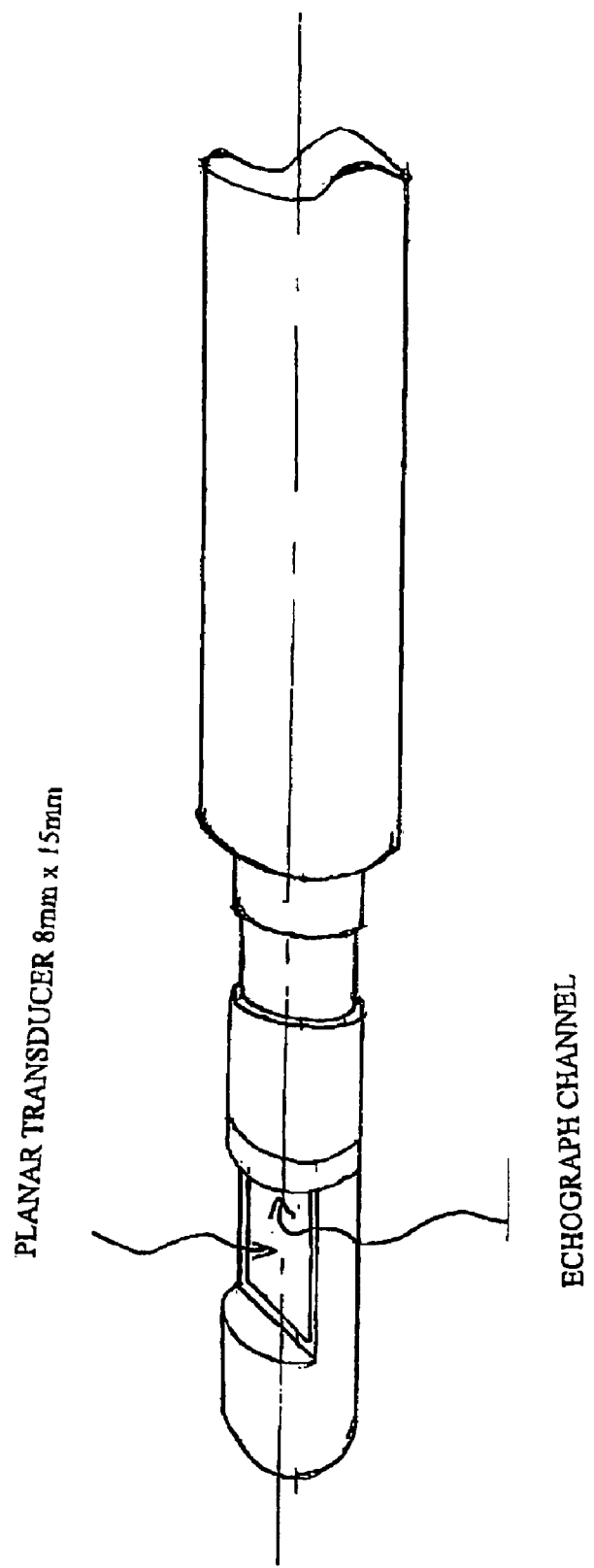

In a fifth embodiment, the invention provides laparoscopic apparatus. This has one or several planar transducers on a probe which may or may not be articulated. FIG. 20 shows a probe with a planar transducer of typical size 8×15 mm. The transducer extends along the median plane of the probe. The probe body has a channel for inserting an angiography ultrasound scanning probe. This allows the treated region to be imaged. One could also provide such a channel in the previous example of a probe with a scalpel.

Figure 21:
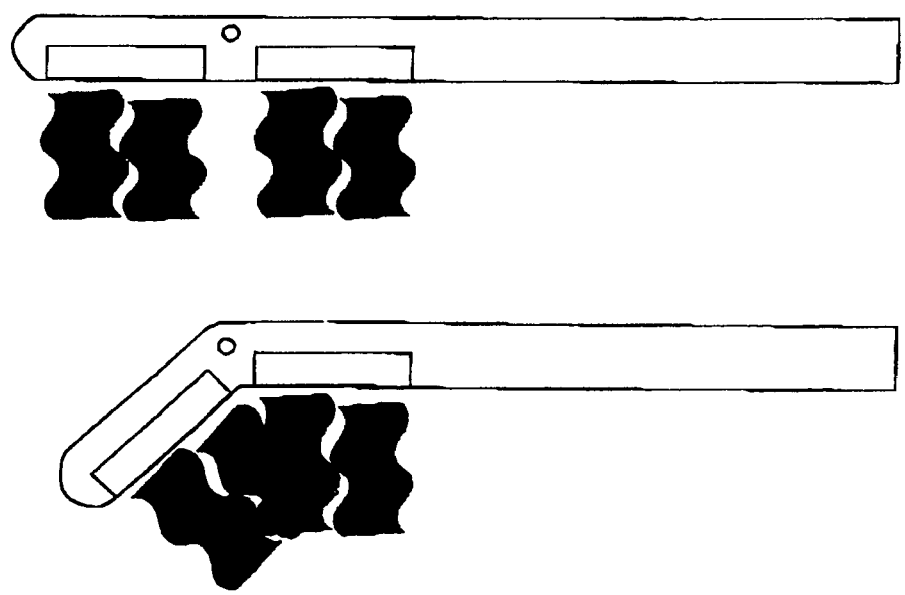
FIGS. 20 to 23 are diagrammatic views of laparoscopic apparatus.

FIG. 21 shows examples of a probe in which several transducers are mounted in line along the probe. Optionally, the probe is articulated thereby allowing:
to better follow the outline of the organ—for example the kidney;
the ultrasound fields to cross thereby increasing energy density at the centre of the kidneys; a focusing effect is achieved; usefully, as planar transducers of significant size are used, treatment depth is significant—at the centre of the kidney, the largest blood vessels are encountered meaning that the power needed for coagulation is greater than at the periphery, which justifies the focusing. "Significant size" means a size of at least 5 mm along the smallest dimension.

Figure 22:
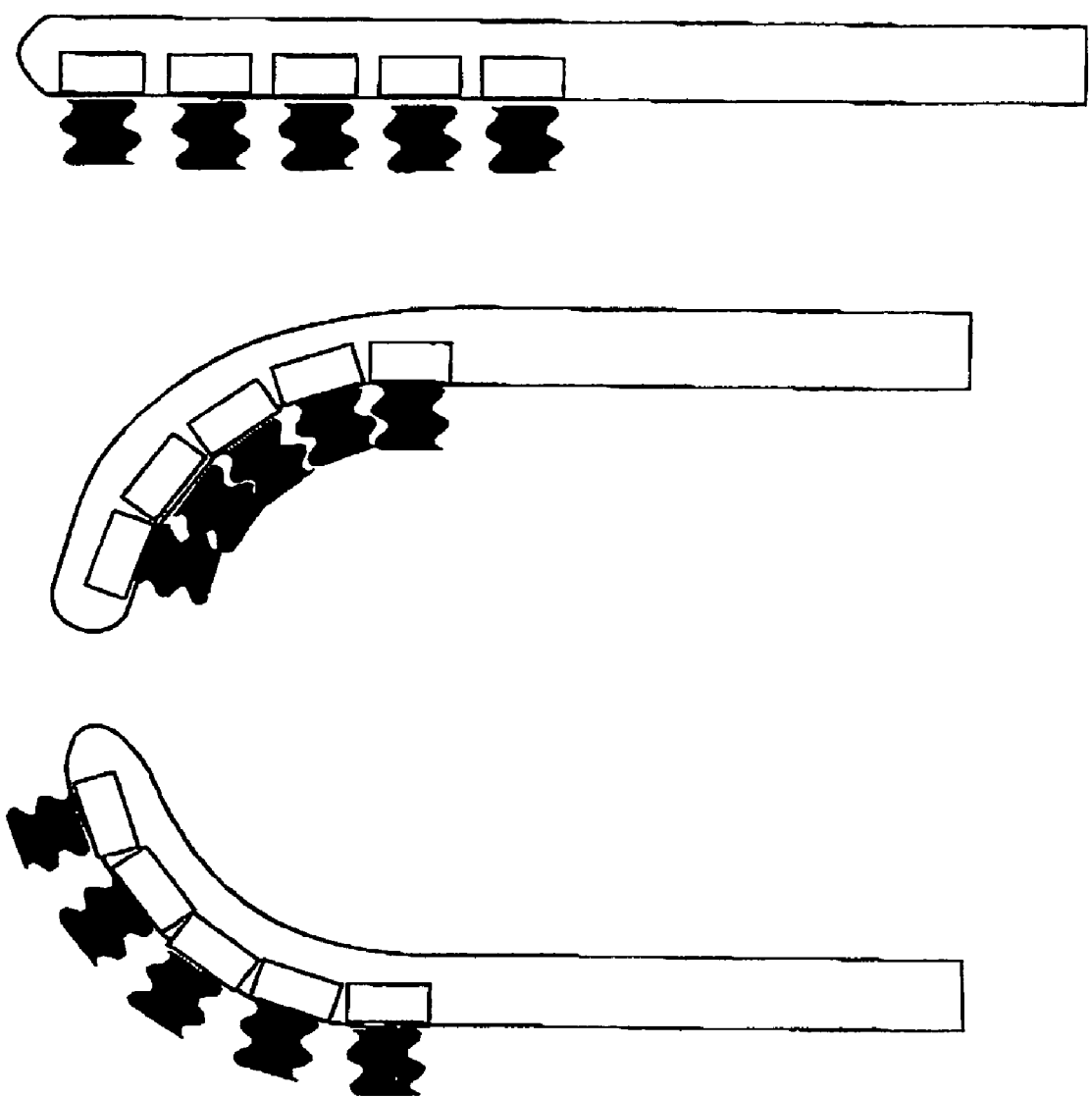

FIG. 22 shows another embodiment, the transducers being smaller and numerous, meaning that the probe is essentially flexible. The advantages discussed above are obtained. Transducer size is now typically less than 5×8 mm. Advantageously, the power of each transducer can be controlled individually.

Figure 23:
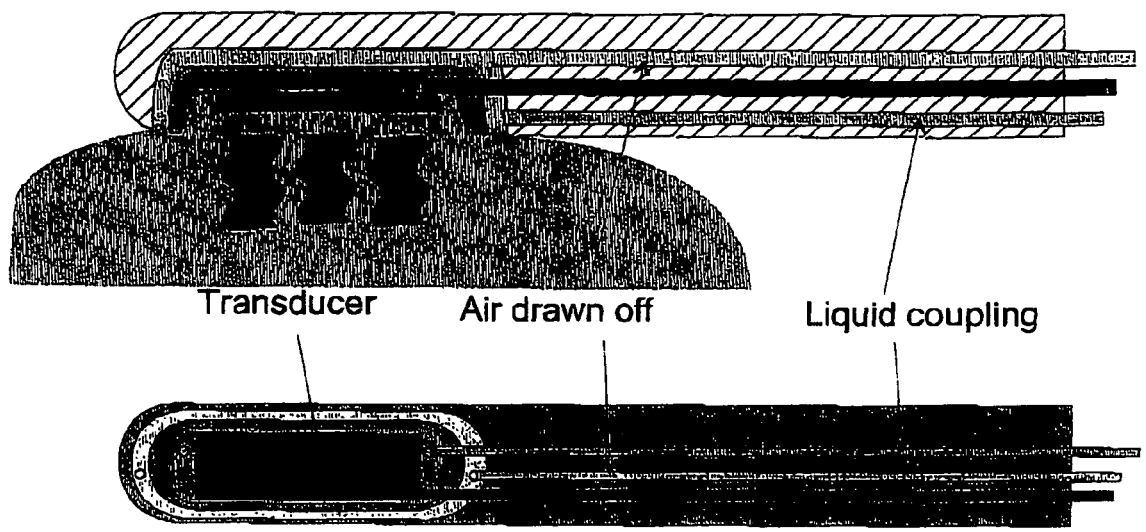

FIG. 23 shows yet a further example in which the probe is held in place on the surface of the kidney by a suction effect. A channel that opens close to the transducer is provided inside which a sub-atmospheric pressure is maintained for holding the probe in place on the kidney. The channel is consequently adapted to transmit a partial vacuum, it being sufficiently rigid. Advantageously, the channel in which a partial vacuum is maintained surrounds the distal portion of the probe. This embodiment can be combined with the various embodiments discussed above. For example, the channel and groove of FIG. 23 can be arranged around the transducers of the articulated probes of FIGS. 21 and 22. The advantage is that the probe is kept in place on the organ despite the latter moving as a result of breathing for example. FIG. 23 also shows that a circuit for coupling and for cooling liquid can be provided. As discussed with reference to FIGS. 1 and 2, the need for a membrane or acoustic window in front of the transducer can be obviated. Such instruments can also be used for coagulating liver tumors.

Pre-clinical trials have been conducted on rabbit livers in-vivo with the following parameters:

frequency: 10 MHz±10 per cent acoustic power: 14 to 18 W/cm$^2$;

duration of shots: 10-40 seconds;

transducer size: 6×10 mm number of shots: 5-7.

The percentage of coagulation of vessels compared to healthy tissue as control was determined.

Figure 24:
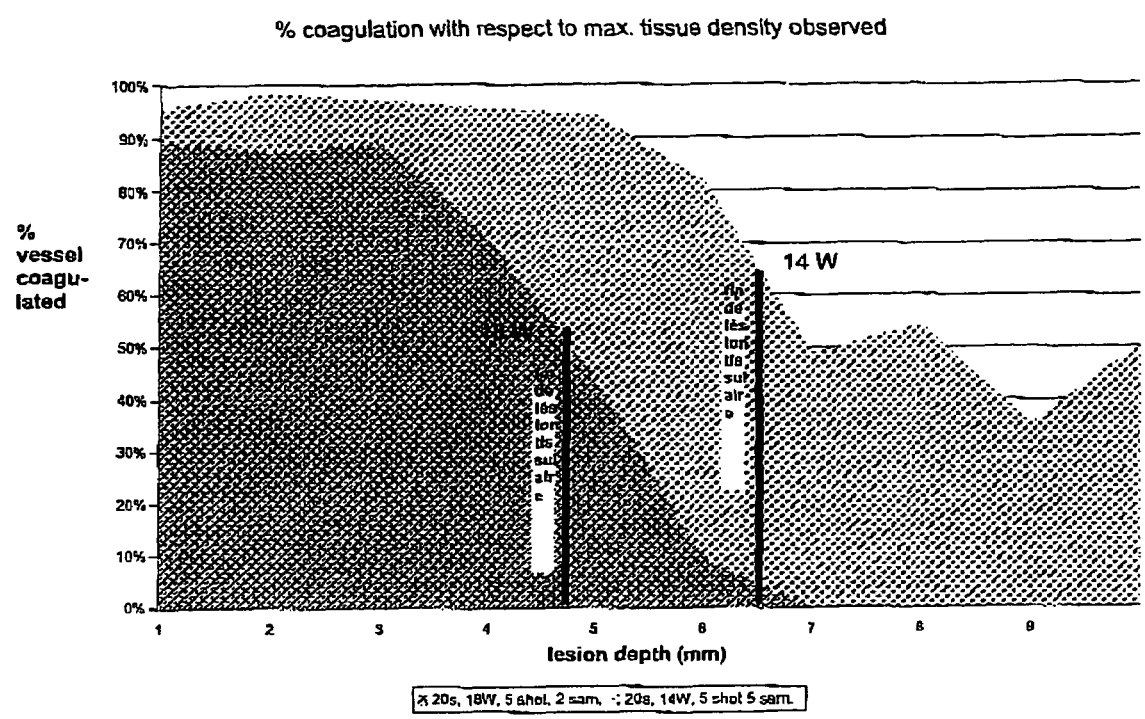
FIGS. 24 and 25 are graphs of experimental results from the use of the invention.

The influence of shooting power can be seen on the graph of FIG. 24 where the effect of variation on firing power on coagulation depth can be seen. The results obtained are as follows: contrary to what was expected, it was observed that increasing ultrasound power limits ultrasound penetration into the tissue. This decrease in lesion size (marked by the indicator for end of lesion on the graph) can be explained by a cavitation phenomenon occurring when tissue temperature rises excessively.

It was also observed that the major portion of vessels located inside the tissue lesion was coagulated for both amounts of acoustic power applied.

To conclude, it is not necessary to increase power excessively as, beyond a certain threshold, the total volume coagulated decreases. One can thus limit coagulation depth by increasing power.

Figure 25:
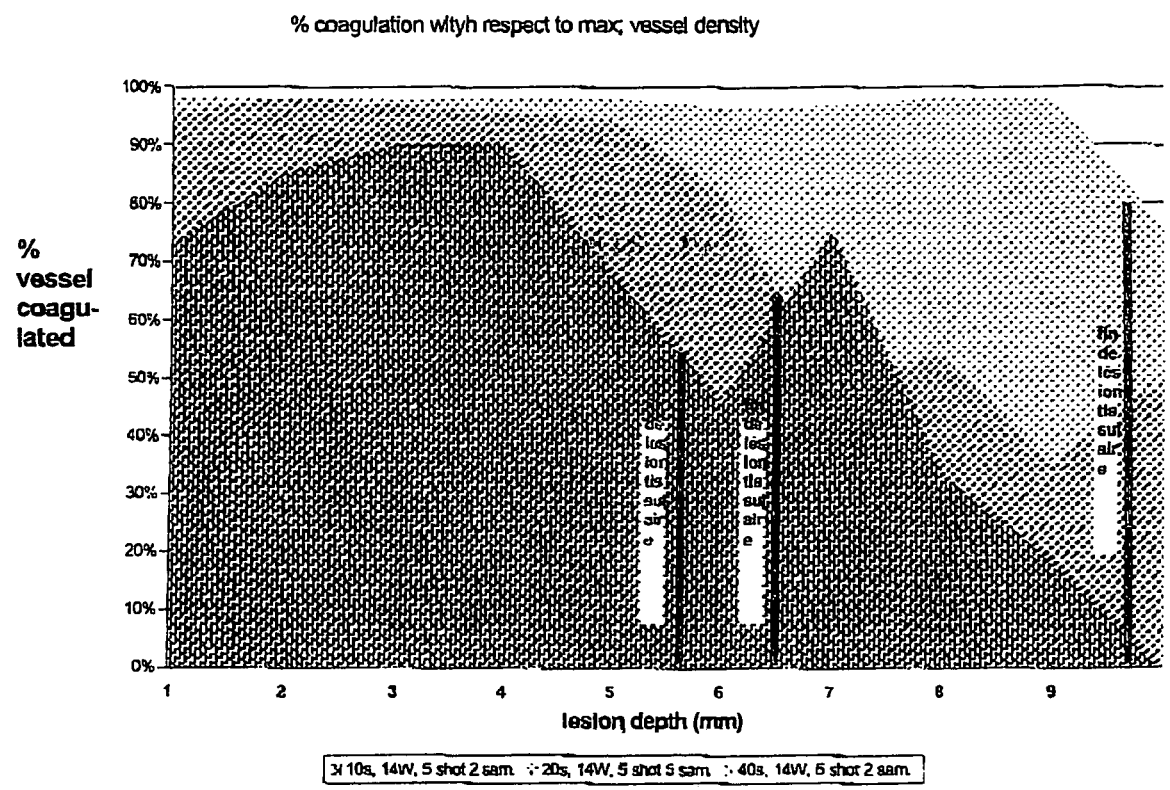

The influence of short duration can be seen on the graph FIG. 25. The second way of interpreting the results consists in observing difference of variations in shot duration. The results obtained are as follows: the acoustic power of 14 W/cm$^2$ was chosen to avoid cavitation phenomenon. It was observed that increasing duration of ultrasound emission increases ultrasound penetration into the tissue. This increase in lesion size is also associated with the histological quality of coagulation. In effect, when firing time is short (10 seconds), a greater number of vessels located in the tissue necrosis region are spared, while for durations of 20 and 40 seconds, all vessels of the lesion region are obstructed. One can consequently regulate depth of coagulation by adjusting firing time.

To conclude, lesion depth is intimately related to ultrasound application time and it is sufficient to provide minimal energy to ensure vessel obstruction, thanks to the shape of the transducer.

Obviously, the invention is not limited to the embodiments which have been described by way of example.

Further, other inventions described above are defined as follows.

A first one provides an endo-urethral probe having, in the region of its extremity, a balloon and a planar ultrasound transducer. Preferred embodiments comprise one or several of the following features:

the probe has a cooling circuit;

the probe has a transducer temperature sensor;

the probe has an interface at an end thereof remote from said transducer, rotation of said interface bringing about rotation of the transducer;

the probe has an imaging transducer; in a particular embodiment, the imaging transducer and the planar transducer are one;

the transducer emits from both faces thereof;

the probe has a plurality of planar transducers; in a particular embodiment, said transducers are mounted along the probe and in another particular embodiment, the transducers are at the same level along said probe;

the probe has a profiled shape, preferably triangular;

the probe has a removable sheath.

Another invention provides an apparatus comprising an endo-urethral probe according to this first other invention, a coupling and cooling fluid circuit associated with said probe, and a radiofrequency generator connected to said probe. In an embodiment, the apparatus is characterized by an imaging generator connected to the imaging transducer of said probe.

A further invention provides a coagulator having a rectoscope tube with an ultrasound transducer at an end of said tube. Preferred embodiments comprise one or several of the following features:

the coagulator has a cooling and coupling fluid circuit with fluid inlet and outlet openings preferably in the region of said transducer;

said transducer is movably mounted with respect to a resection device; in a particular embodiment thereof, said transducer is mounted on hinged fastening lugs;

the coagulator further comprises a resection loop;

the transducer has a shape adapted to said resection loop;

the transducer is movable with respect to said resection loop;

the transducer and the resection loop are powered by the same cable;

the transducer is a planar transducer.

What is claimed is:

1. A laparoscopy probe comprising:

a fluid source arranged to provide a coupling fluid, at least one planar ultrasound transducer arranged for emitting a coagulating ultrasound beam such that the ultrasound beam is transmitted only through the coupling fluid; and a channel that opens in the region of said transducer, adapted to transmit a partial vacuum for keeping the laparoscopy probe in place on an organ when emitting the coagulating ultrasound beam to the organ with the at least one planar ultrasound transducer.

2. The probe of claim 1, comprising a probe body wherein the probe body has a channel for inserting an ultrasound angiography probe.

3. The probe of claim 2, comprising a plurality of transducers and a flexible or articulated body.

4. The probe of claim 2, wherein the opening of said channel surrounds the transducer.

5. The probe of claim 1, wherein the opening of said channel surrounds the transducer.

6. The probe of claim 1, comprising a plurality of transducers and a flexible or articulated body.

7. The probe of claim 1, further comprising a scalpel blade, wherein said scalpel blade is movable with respect to said transducer.

8. An ultrasound coagulation apparatus, comprising:
a fluid source arranged to provide a coupling fluid,
an ultrasound transducer arranged for emitting a coagulating ultrasound beam along a path towards a target to be coagulated such that the ultrasound beam is transmitted only through the coupling fluid, and
a scalpel blade, and
said scalpel blade is movable with respect to said transducer when the ultrasound coagulation apparatus is in operation.

9. The apparatus of claim 8, further comprising an imaging transducer.

10. A coagulation instrument comprising:
a planar ultrasound transducer,
a fluid source arranged to provide a coupling fluid,
a cable, in which;
the planar ultrasound transducer is mounted in the region of an end of the cable,
said planar ultrasound transducer is arranged for emitting a coagulating ultrasound beam along a path towards a target to be coagulated such that the ultrasound beam is transmitted only through the coupling fluid;
said planar transducer is powered via said cable; and
said cable and said planar ultrasound transducer form an assembly adapted to pass in an operating channel of an endoscopic apparatus.

11. The coagulation instrument of claim 10, wherein the coagulation instrument has a diameter less than 1 to 5 mm.

12. The coagulation instrument of claim 11, wherein the cable is flexible.

13. The coagulation instrument of claim 10, wherein the cable is flexible.

14. An endoscopic apparatus comprising:
a coagulation instrument having a planar ultrasound transducer without a membrane, mounted in the region of an end of a cable, and
a fluid source arranged to provide a coupling fluid,
a cooling and coupling fluid circuit, with fluid inlet and outlet openings, in which:
said planar ultrasound transducer is arranged for emitting a coagulating ultrasound beam along a path toward a target to be coagulated such that the ultrasound beam is transmitted only through the coupling fluid;
said planar ultrasound transducer is powered via said cable; and
said cable and said planar ultrasound transducer form an assembly adapted to pass in an operating channel of the endoscopic apparatus.

15. The endoscopic apparatus of claim 14, wherein the fluid inlet and outlet openings are in the region of the transducer.

16. The endoscopic apparatus of claim 14, wherein the coagulation instrument has a diameter less than 1 to 5 mm.

17. The endoscopic apparatus of claim 14, wherein the cable is flexible.

18. The endoscopic apparatus of claim 14, wherein the transducer is in the region of a free end of the apparatus.

19. A laparoscopy probe having comprising at least one planar ultrasound transducer without a membrane and a fluid source arranged to provide a coupling fluid, in which said planar ultrasound transducer is arranged for emitting a coagulating ultrasound beam along a path toward a target to be coagulated such that the ultrasound beam is transmitted only through the coupling fluid.

* * * * *